United States Patent [19]
Funatogawa

[11] Patent Number: 5,076,263
[45] Date of Patent: Dec. 31, 1991

[54] TOE STRETCHER

[76] Inventor: Hiroyuki Funatogawa, 3208-1 Tori 5-chome, Ashikaga-City, Tochigi-Prefecture, Japan

[21] Appl. No.: 410,827
[22] Filed: Sep. 22, 1989
[51] Int. Cl.$^5$ .............................................. A61F 5/00
[52] U.S. Cl. ................................ 128/81 R; 132/73; 272/139; 272/96
[58] Field of Search ............... 272/67, 68, 96, 139; 128/0.80 R, 0.81 R; 132/73, 73.5, 285

[56] References Cited

U.S. PATENT DOCUMENTS

| | | | |
|---|---|---|---|
| 1,624,171 | 4/1927 | Johnson | 128/81 R |
| 2,471,997 | 5/1949 | Baltor | 132/73 X |
| 2,517,232 | 11/1950 | Patulski | 132/73 |
| 2,531,851 | 11/1950 | Kinad | 128/81 R |
| 2,751,693 | 6/1956 | Baker | 132/73 |
| 2,949,112 | 8/1960 | Murray | 128/81 R |
| 3,049,120 | 8/1962 | Marcus | 128/81 R |

FOREIGN PATENT DOCUMENTS

| | | | |
|---|---|---|---|
| 0276558 | 7/1914 | Fed. Rep. of Germany | 132/73 |
| 1095213 | 12/1954 | France | 132/73 |
| 0525059 | 8/1940 | United Kingdom | 132/73 |

OTHER PUBLICATIONS

*Websters New World Dictionary; Third College Edition* Copyright 1988; p. 701.

*Primary Examiner*—Richard J. Apley
*Assistant Examiner*—L. Thomas
*Attorney, Agent, or Firm*—Lorusso & Loud

[57] ABSTRACT

A toe stretcher comprising stretching posts stood upright at positions corresponding to spacings between toes, the stretching posts being formed of an elastic material having a diameter capable of spreading a portion between toes on a base plate of the size capable of putting the tip of toes thereon.

4 Claims, 4 Drawing Sheets

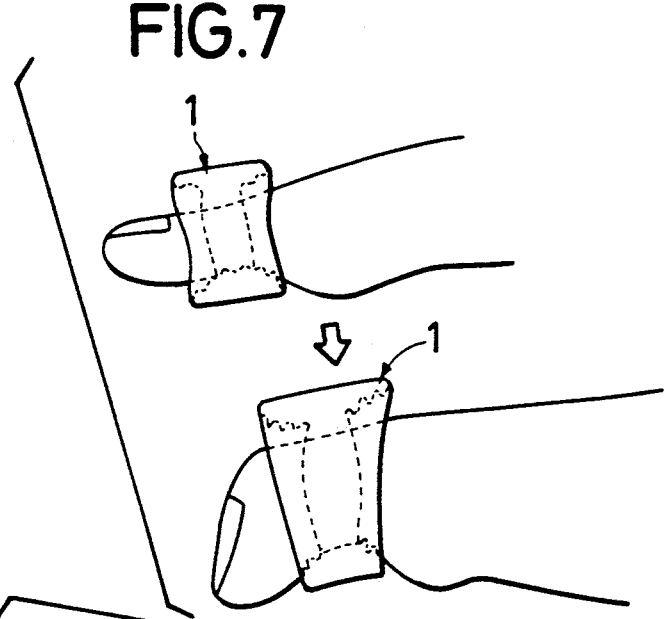
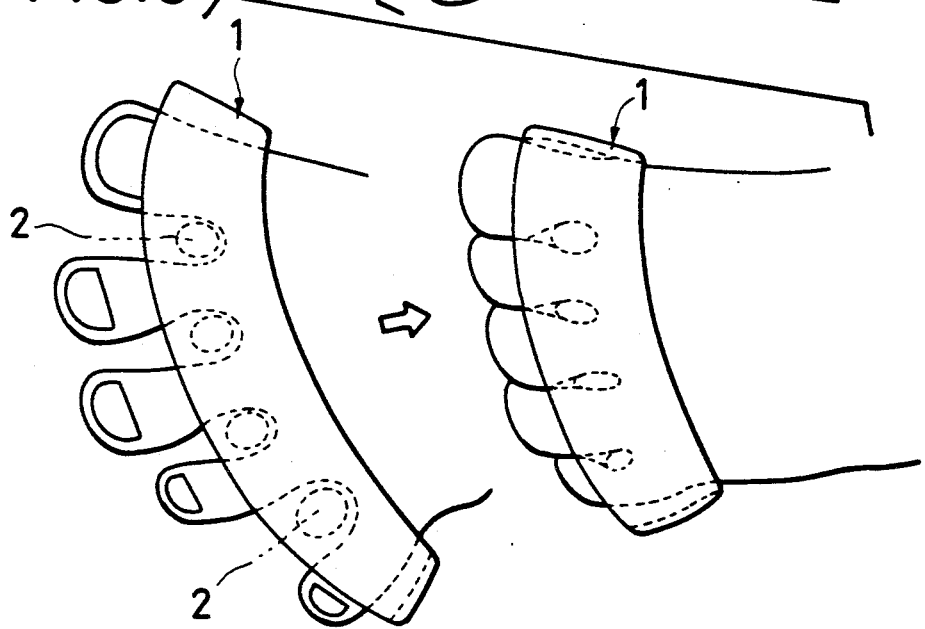

TOE STRETCHER

BACKGROUND OF THE INVENTION

1. Field of the Invention

The present invention relates to a toe stretcher which is held between toes to maintain toes at wide angles so as to massage the portions between toes as well as strengthening of toes, and principally to a toe stretcher which can be readily used in places where shoes are taken off, for example, such as home, athletic clubs, hospitals, etc., and which can walk while putting on shoes depending on the thickness of material.

2. Description of the Prior Art

In the past, man could move on the ground freely using five toes. However, with the recent development of automobiles, automation of all the things have been spread to save the time that man uses toes. Therefore, man become hard to walk with their toes firmly placed on the ground. Of course, the cause thereof resides in pavement of most roads but a progress in function of shoes gives impetus to this state, and a change in fashionability involves. The former extremely reduces a burden applied to toes while the latter applies an unnatural burden to feet. Thereby, partly, it is a matter of the fact that cannot be overlooked that the above phenomena results in progress of weakening feet. Particularly, in high heels of women and other shoes in which toes are tightened, freedom of toes is impaired, and the circulation of blood of toes is also always impaired. Furthermore, a middle toe bone or a toe bone is being weakened.

It is therefore necessary to stretch toes in order to prompt activation of toes. However, in the past, one's own hands or others' hands have been used as in the finger-pressure in order to stretch toes.

SUMMARY OF THE INVENTION

It is an object of the present invention to provide a toe stretcher which, in a still state, can spread a portion between toes without requiring a special force of man, and provide an effect during walking operation, and apply a stimulus similar to a bamboo-stepping effect over and between the tip to the root of the toe (particularly in toe bone portion, the base and middle portions), and which can be used for all fields of people who daily use shoes and various hospitals and the like.

For achieving the aforesaid object, there is provided a toe stretcher having stretching posts stood upright at positions corresponding to spacing between toes, the stretching posts formed of elastic material having a diameter capable of spreading a portion between toes on a base plate of the size capable of placing toes thereon.

BRIEF DESCRIPTION OF THE DRAWINGS

FIG. 7 is an observation view viewed from the side in case where stretching motion according to the present invention is effected;

FIG. 8 is an observation view viewed from the top;

DETAILED DESCRIPTION OF THE PREFERRED EMBODIMENTS

Preferred embodiments will be described in detail with reference to the drawings.

Figure 1:
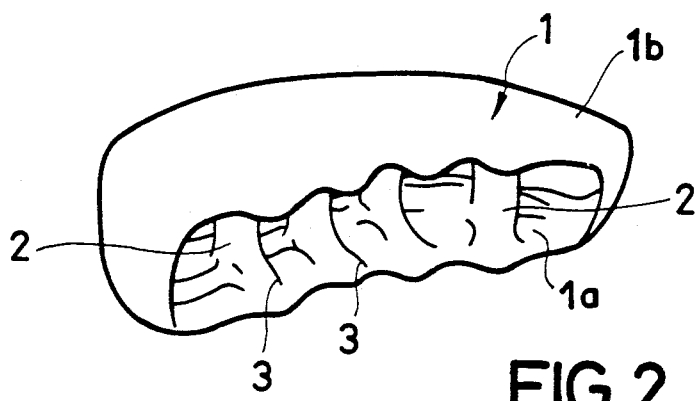
FIG. 1 is a perspective view showing one embodiment.

FIG. 1 is a perspective view showing one embodiment of the present invention and corresponds to the invention in claim 2.

Stretching posts 2 formed of an elastic material having a diameter capable of spreading a portion between toes are stood upright between upper and lower portions of a base frame 1 capable of receiving the tip of toe and having an elasticity.

Optimum material for the base frame 1 is an expansible independent foam material or material having the nature similar thereto.

Figure 3:
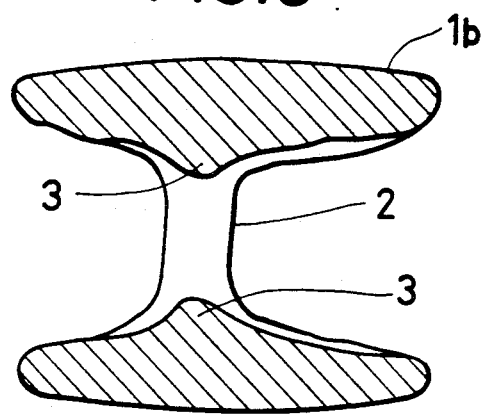
FIG. 3 is a sectional view in a vertical direction of the same.

The surface of the base frame 1 is formed with a thick wall portion 3 protruded toward the stretching post 2 as shown in FIG. 3 which is a vertical sectional view. The thick wall portion 3 is provided not only to spread a portion between toes by the stretching post 2 but to press and stimulate the portion between the toes.

Figure 4:
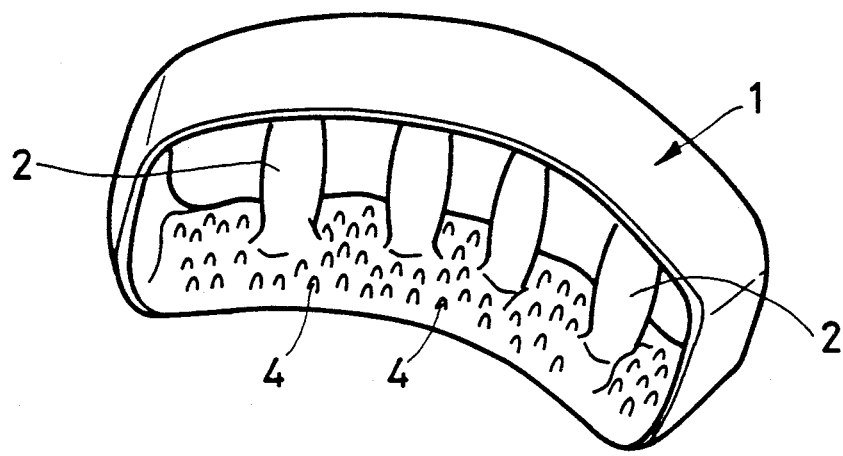
FIG. 4 is a perspective view showing a further embodiment in which a stimulus projection is formed internally of a base frame.
Figure 5:
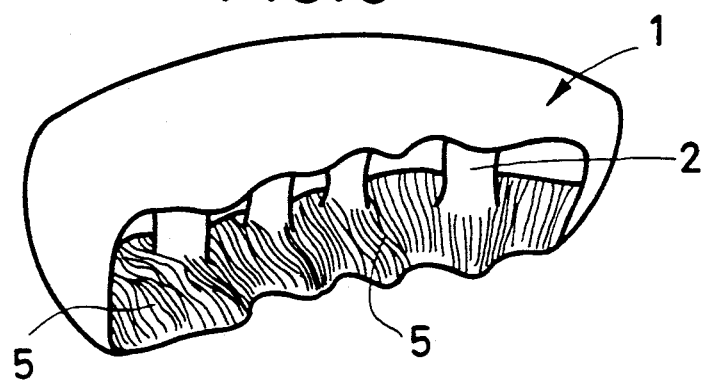
FIG. 5 is a perspective view showing another embodiment in which a stimulus groove is formed internally of a base frame.

The base frame 1 can be formed internally with a stimulative concave-convex portion to give a stimulus to the skin of the tip of toe. The stimulative concave-convex portions are obtained by standing upright a number of projections as shown in FIG. 4, and forming longitudinal stripe-like grooves 5 as shown in FIG. 5.

Figure 2:
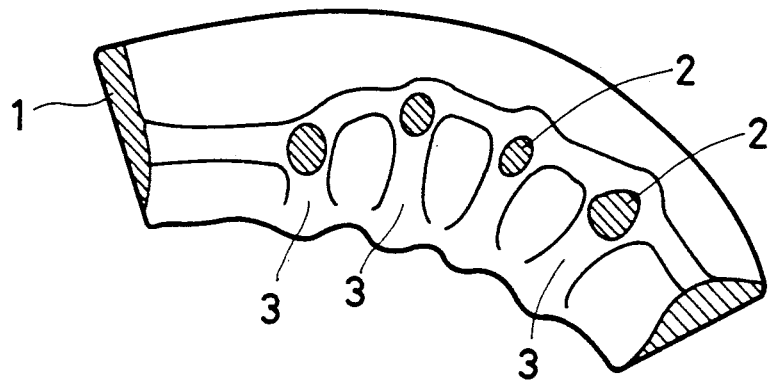
FIG. 2 is a sectional view in a horizontal direction of the same.

Four stretching posts 2 are stood upright at positions corresponding to the spacing between the toes as shown in FIG. 2, which is a horizontal sectional view, and formed of the same material as that of the base frame 1, the posts 2 being formed integral with the base frame 1.

As the result, the stretching posts 2 may enter between five base bones even in the toe bones. However, the case of corresponding to the middle bone except the big toe can be considered.

Figure 6:
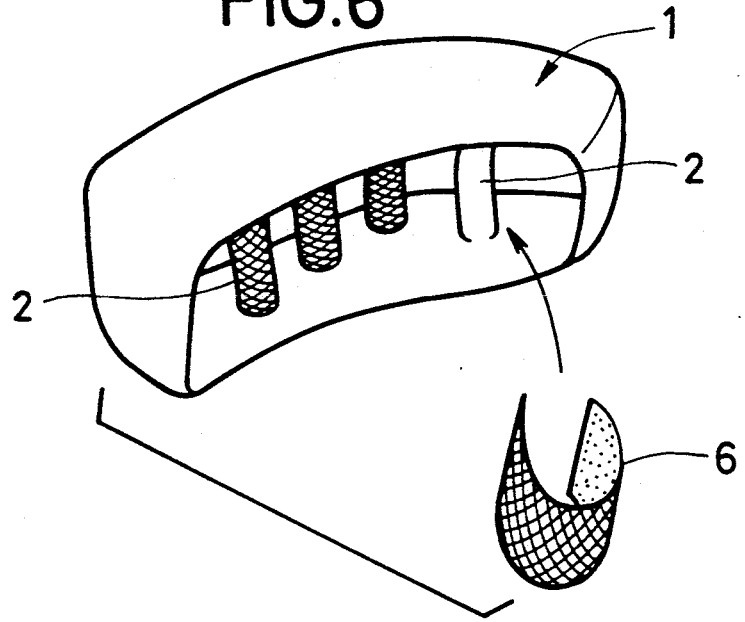
FIG. 6 is a perspective view in a state wherein a natural fiber is wound about a stretching post.

One using a natural fiber as the material for the stretching post 2 and one having a fiber 6 of natural material wound on the skin as shown in FIG. 6 can give a stimulus between the toes and a favorable feeling to attachment of the toe stretcher.

Figure 9:
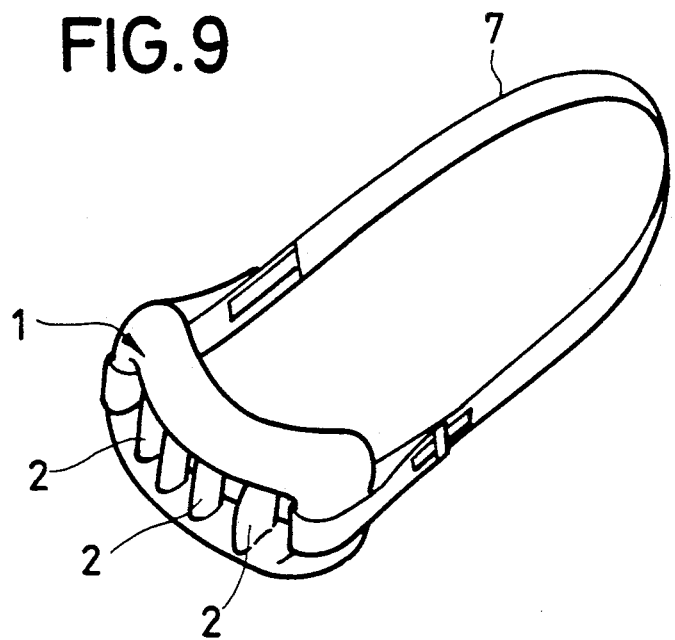
FIG. 9 is a view in which a falling-down preventive belt is mounted on a toe stretcher.
Figure 10:
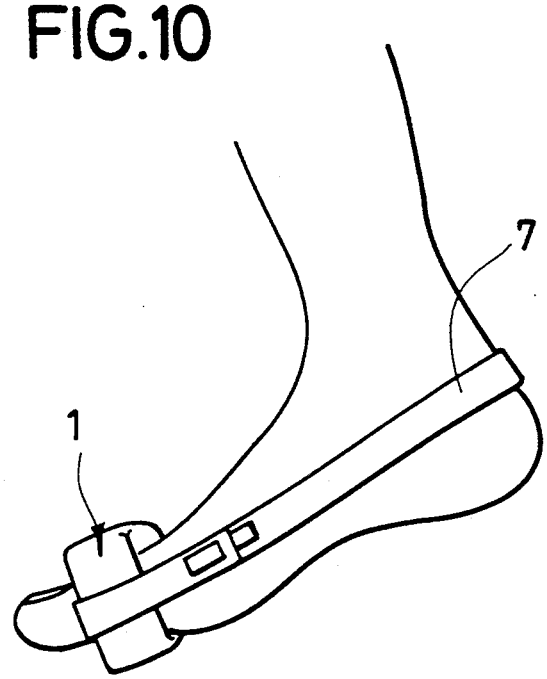
FIG. 10 is a view showing a state in which a toe stretcher with a falling-down preventive belt is attached to the foot.

FIG. 9 is a view in which a falling-down preventive belt is mounted on a toe stretcher. FIG. 10 is a view showing a state in which a toe stretcher with a falling-down preventive belt is attached to the foot. This belt 7 has a function of adjusting a length and is formed of an expansible material such as a flat rubber to enhance a fitness.

In the present embodiment, a pair of symmetrical left and right portions are provided.

In the present invention, as shown in the upper portion of FIG. 8, in the barefoot, the stretching posts 2 are placed to be sandwiched between the toes of both feet.

Even in this still state, the toes and the portion therebetween can be equally pressed to forcibly spread the portion between the toes.

In addition, since the stretching posts 2 and the base frame 1 are formed of elastic material, the muscular power of the toes can be strengthened by flexing the toes as shown in the lower part of FIG. 7 after the toes stretcher has been attached.

FIG. 7 is a view of the flexing state as viewed from the side of the foot. FIG. 8 is a view of the flexing state as viewed from the top of the foot.

Since this device utilizes the construction of toes and the principle of motion thereof, the attached toe stretcher can be used without being disengaged during walking operation. During walking, the spreading motion of the toes is promoted without requiring a special force, and the effect similar to bamboo stepping from the tip of toe to the root of toe (particularly in the toe bone portion, the base and middle bone portions) is attained.

What is claimed is:

1. A toe stretcher for stimulating the toes of a users foot, said toe stretcher comprising a frame in the form of a continuous band including upper and lower runs and surrounding the toes, four upright posts secured to and bridging said upper and lower runs at positions corresponding to spacings between the toes of the foot and ridges sloping toward said posts, said ridges being integral with the interior of said band, said posts having a sufficiently large diameter to forcibly spread the toes upon insertion of the toes into the toe stretcher, said band being of a sufficiently narrow width to allow the toes, upon insertion, to extend through and substantially beyond said band.

2. The toe stretcher of claim 1 wherein said band and said posts are integrally formed.

3. The toe stretcher of claim 2 wherein said band and said posts are formed of an elastomeric material.

4. The toe stretcher of claim 1 further comprising a strap for passing around the heel of the user for holding the toe stretcher on the toes.

* * * * *